US00PP08770P

United States Patent [19]

Hesse

[11] Patent Number: Plant 8,770

[45] Date of Patent: Jun. 7, 1994

[54] CHRYSANTHEMUM PLANT 'RAGE'

[75] Inventor: Peter S. Hesse, Nipomo, Calif.

[73] Assignee: Clearwater Nursery, Inc., Nipoma, Calif.

[21] Appl. No.: 57,961

[22] Filed: May 5, 1993

[51] Int. Cl.[5] ..... A01H 5/00

[52] U.S. Cl. ..... Plt./82.5

[58] Field of Search ..... Plt. 82.5

*Primary Examiner*—James R. Feyrer

*Attorney, Agent, or Firm*—Arnold, White & Durkee

[57] ABSTRACT

The present invention comprises a new and distinct cultivar of Chrysanthemum, botanically known as *Dedranthema grandiflora,* and referred to by the cultivar name Rage in North America. Rage is distinguished by its bright red floret color and long shelf life.

1 Drawing Sheet

BACKGROUND OF THE NEW PLANT

Rage was identified as P89-001 originated from a cross made by Peter S. Hesse in a controlled breeding program at Clearwater Nursery, Nipomo, Calif. 98444, USA.

The female parent of Rage was Lucido (U.S. Plant Pat. No. 6,586), and the male parent was Stop Light (U.S. Plant Pat. No. 5,721). Rage was discovered and selected as a flowering plant in October 1989, at Clearwater Nursery, Nipomo, Calif. by Peter S. Hesse in a controlled Greenhouse environment.

The first act of asexual reproduction of Rage was accomplished in March of 1990, when vegetative cuttings were taken in a controlled greenhouse environment at Clearwater Nursery, Nipomo, Calif., by technicians working under the direction of Peter S. Hesse.

Horticultural examination of controlled flowerings of successive plantings has shown that the unique combination of characteristics as herein disclosed for Rage are firmly fixed and are retained through successive generations of asexual reproduction.

Rage has not been observed under all possible environmental conditions. The phenotype may vary significantly with variations in environment such as temperature, light intensity and day length.

The following observations, measurements and comparisons describe plants grown in controlled greenhouse environments at Clearwater Nursery, Nipomo, Calif. Unrooted cuttings were directly stuck into 6.5 inch pots and grown in a controlled environment under the natural temperature and day length prevailing June 1990 to December 1992.

The following traits have been repeatedly observed and are determined to be basic characteristics of Rage which, in combination distinguish this Chrysanthemum as a new and distinct cultivar.

1. Flat Capitulum Form
2. Daisy Capitulum Type
3. Very bright red ray florets under fluorescent lights.
4. Shiny green foliage color.
5. A diameter of 7.8 cm across the face of the capitulum.
6. An average of 9.0 flowers per break.
7. Excellent upright spreading habit with an average of 5.2 breaks after a single pinch.
8. An average flowering response to 59 days from the start of short days.

DESCRIPTION OF THE PHOTOGRAPH

The accompanying photograph shows typical inflorescence and leaf characteristics of Rage with the colors being as nearly true as possible with illustrations of this type. The photograph shows Rage grown as a pinched spray pot mum with five (5) cuttings in a 6.5 inch pot.

DESCRIPTION OF THE PLANT

Of the commercial cultivars known to the inventors, the most similar in comparison to Rage is the cultivar identified as Lucido (U.S. Plant Pat. No. 6,586). Reference is made to Table I which compares certain characteristics of Rage to the same characteristics of Lucido.

TABLE I

| CHARACTERISTIC | RAGE | LUCIDO |
|---|---|---|
| CAPITULUM FORMS | Flat | Flat |
| CAPITULUM TYPE | Daisy | Daisy |
| DIAMETER ACROSS FACE | 7.8 cm | 7.0 cm |
| BRANCHING PATTERN | Upright Spreading | Upright Spreading |
| BREAKS/PINCH | 5.2 | 5.4 |
| HEIGHT IN 6.5" POT WITH 1-2 APPLICATIONS B-9 | 16-17 Inches | 16-17 Inches |
| DISC FLORETS | | |
| DISC FLORET COLOR | 13A | 13A |
| NO. OF DISC FLORETS | Many | Many |
| LENGTH OF DISC FLORETS | ca 0.72 cm | ca 0.64 cm |
| RAY FLORETS | | |
| COLOR | | |
| FRONT: fully expanded | 46A | 46A |
| FRONT: unfolded ray florets | 46A | 46A |
| BACK: fully expanded outer ray floret | 172B | 46B |
| NUMBER | 33.4 | 28.8 |
| SHAPE | Elliptic | Elliptic |
| LENGTH | 3.7 cm | 3.3 cm |
| WIDTH | 1.1 cm | 0.85 cm |
| TOTAL NUMBER OF FLOWERS/BREAK | 9.0 | 12.6 |
| LEAF | | |
| COLOR: | Front: 147A Back: 147B | Front: 147A Back: 147B |
| MATURE LEAF LENGTH: | 9.9 cm | 9.03 cm |
| MATURE LEAF WIDTH: | 5.7 cm | 4.56 cm |

Rage is similar to Lucido in the flat capitulum form and the daisy capitulum type. The diameter across the capitulum is essentially the same. Rage has a more upright habit than Lucido. The Number of breaks per pinch is essentially the same for Rage and for Lucido. Disc floret color is also similar. One big difference between Rage and Lucido is the brightness of the red ray floret color. This is particularly noticeable when both plants are placed side by side and compared under fluorescent lights. Lucido appears darker red and more towards blue or black. Because Rage has more background yellow pigment in the floret, Rage appears brighter red more towards orange. This improves the floral display of Rage at the super market. Rage has more substance than Lucido's ray florets. Rage has more ray florets per capitulum than Lucido. This gives Rage a better shelf life and the brighter red color makes Rage a unique red daisy pot mum.

THE PLANT

Classification:

*Botanical.*—*Dedranthema grandiflora.* Cultivar name: Rage.

*Commercial.*—Flat daisy to be grown as a 4.5" to 6.5" CBR mum.

Inflorescence:

*Capitulum.*—Form: Flat. Type: Daisy. Diameter across face: 7.8 cm.

*Ray florets.*—Color: Red (general tonality within a distance of three (3) meters). Front: Fully expanded outer ray floret 46A. Front: Unfolded ray florets in center of flower 46A. Back: Fully expanded outer ray floret 172B. Front Bud Stage: Unexpanded outer ray floret. Back Bud Stage: Unexpanded outer ray floret. Shape: Elliptic.

*Corolla of disc florets.*—Color: Yellow 13A.

Reproductive organs:

*Androecium.*—Present in disc floret only.

*Gynoecium.*—Present in both ray and disc florets.

General appearance:

*Height.*—When grown in a 6.5 inch pot with 1–2 applications of B-NINE TM at the rate of 2500 ppm, the total plant height from the bottom of the pot may be maintained at 16–18 inches. When grown in a 4.5 inch pot with 1–5 applications of B-NINE TM at the rate of 2500 ppm the total plant height from the bottom of the pot may be maintained at 10–12 inches. Branching pattern: Upright and spreading with an average of 5.2 breaks when grown with one pinch as a spray pot.

*Foliage.*—Color: (upper surface) 147A. Color: (lower surface) 147B. Shape: (see photograph).

What is claimed is:

1. A new and distinct Chrysanthemum plant substantially as herein described and shown, characterized by its bright red color and excellent upright spreading habit.

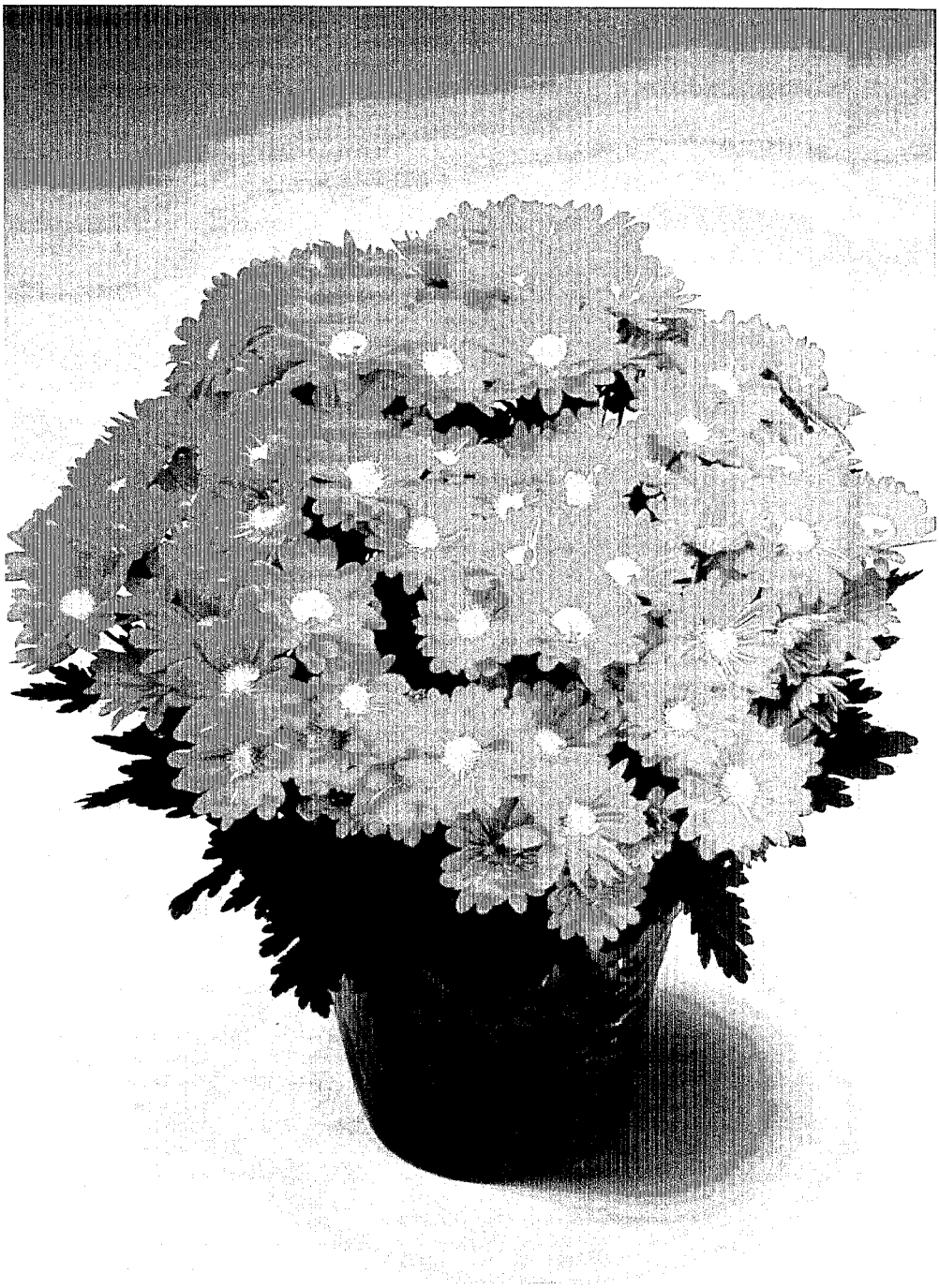

* * * * *